US011123200B2

(12) United States Patent
Faulhaber

(10) Patent No.: US 11,123,200 B2
(45) Date of Patent: Sep. 21, 2021

(54) VARIABLE LORDOTIC INTERBODY SPACER

(71) Applicant: GLOBUS MEDICAL, INC., Audubon, PA (US)

(72) Inventor: Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 6 days.

(21) Appl. No.: 16/513,913

(22) Filed: Jul. 17, 2019

(65) Prior Publication Data

US 2019/0358049 A1 Nov. 28, 2019

Related U.S. Application Data

(60) Division of application No. 15/817,793, filed on Nov. 20, 2017, now Pat. No. 10,390,964, which is a continuation of application No. 14/741,939, filed on Jun. 17, 2015, now Pat. No. 9,848,996.

(51) Int. Cl.
*A61F 2/44* (2006.01)
*A61F 2/30* (2006.01)

(52) U.S. Cl.
CPC ............ *A61F 2/447* (2013.01); *A61F 2/4455* (2013.01); *A61F 2002/3093* (2013.01); *A61F 2002/30182* (2013.01); *A61F 2002/30471* (2013.01); *A61F 2002/30507* (2013.01); *A61F 2002/30538* (2013.01); *A61F 2002/30579* (2013.01); *A61F 2002/30593* (2013.01); *A61F 2002/30787* (2013.01)

(58) Field of Classification Search
CPC .................. A61F 2/44–447; A61F 2002/30507
See application file for complete search history.

(56) References Cited

U.S. PATENT DOCUMENTS

| | | | |
|---|---|---|---|
| 4,349,921 A | 9/1982 | Kuntz | |
| 4,599,086 A | 7/1986 | Doty | |
| 4,863,476 A | 9/1989 | Shepperd | |
| 4,863,477 A | 9/1989 | Monson | |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Nicholas J Plionis

(57) ABSTRACT

A variable lordotic interbody spacer including a face plate, superior and inferior endplates coupled to the face plate via a hinge, an actuation frame between the endplates, and an actuation screw. The face plate includes actuation and stabilizer channels. Each of the endplates has endplate arms coupled by an endplate base, and includes actuation ramp recesses. The actuation frame includes frame arms coupled by a frame base in a generally U-shaped configuration, each actuation frame arm having a stabilizer feature passing through a corresponding stabilizer channel and having actuation ramp pins fitted to a corresponding ramp recesses. The actuation screw passes through the actuation channel, with a head retained at the front surface and a threaded end coupled to the actuation frame. When operated, the actuation screw moves the actuation frame between the superior endplate and the inferior endplate to adjust an angle therebetween.

15 Claims, 13 Drawing Sheets

(56) References Cited

U.S. PATENT DOCUMENTS

| | | |
|---|---|---|
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 8,123,810 B2 | 2/2012 | Gordon |
| 8,647,386 B2 | 2/2014 | Gordon |
| 8,685,095 B2 | 4/2014 | Miller et al. |
| 2002/0045945 A1 | 4/2002 | Liu |
| 2004/0049271 A1 | 3/2004 | Biedermann |
| 2004/0054412 A1 | 3/2004 | Gerbec et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0058878 A1 | 3/2006 | Michelson |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270965 A1* | 11/2007 | Ferguson ........... A61B 17/7059 623/17.11 |
| 2007/0270968 A1 | 11/2007 | Baynham |
| 2007/0282441 A1* | 12/2007 | Stream ................ A61F 2/30771 623/17.11 |
| 2008/0021559 A1 | 1/2008 | Thramann |
| 2008/0065222 A1 | 3/2008 | Hamada |
| 2008/0140207 A1 | 6/2008 | Olmos et al. |
| 2008/0167657 A1 | 7/2008 | Greenhalgh |
| 2008/0183204 A1 | 7/2008 | Greenhalgh et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0168859 A1 | 7/2010 | Wardlaw |
| 2010/0179657 A1 | 7/2010 | Greenhalgh et al. |
| 2010/0185289 A1* | 7/2010 | Kirwan ................ A61F 2/4455 623/17.11 |
| 2011/0153020 A1 | 6/2011 | Abdelgany et al. |
| 2012/0109308 A1 | 5/2012 | Lechmann et al. |
| 2012/0185049 A1 | 7/2012 | Varela |
| 2013/0158663 A1 | 6/2013 | Miller et al. |
| 2014/0067071 A1* | 3/2014 | Weiman ................ A61F 2/442 623/17.16 |
| 2014/0228957 A1* | 8/2014 | Niemiec ............ A61B 17/8605 623/17.16 |
| 2014/0277489 A1 | 9/2014 | Davenport et al. |
| 2016/0166396 A1* | 6/2016 | McClintock ........ A61F 2/30771 623/17.16 |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| JP | 2005509487 A | 4/2005 |
| JP | 2015500706 A | 1/2015 |
| SU | 1424826 A1 | 9/1988 |
| WO | 9201428 A1 | 2/1992 |
| WO | 9525485 A1 | 9/1995 |
| WO | 2014151172 A1 | 9/2014 |

\* cited by examiner

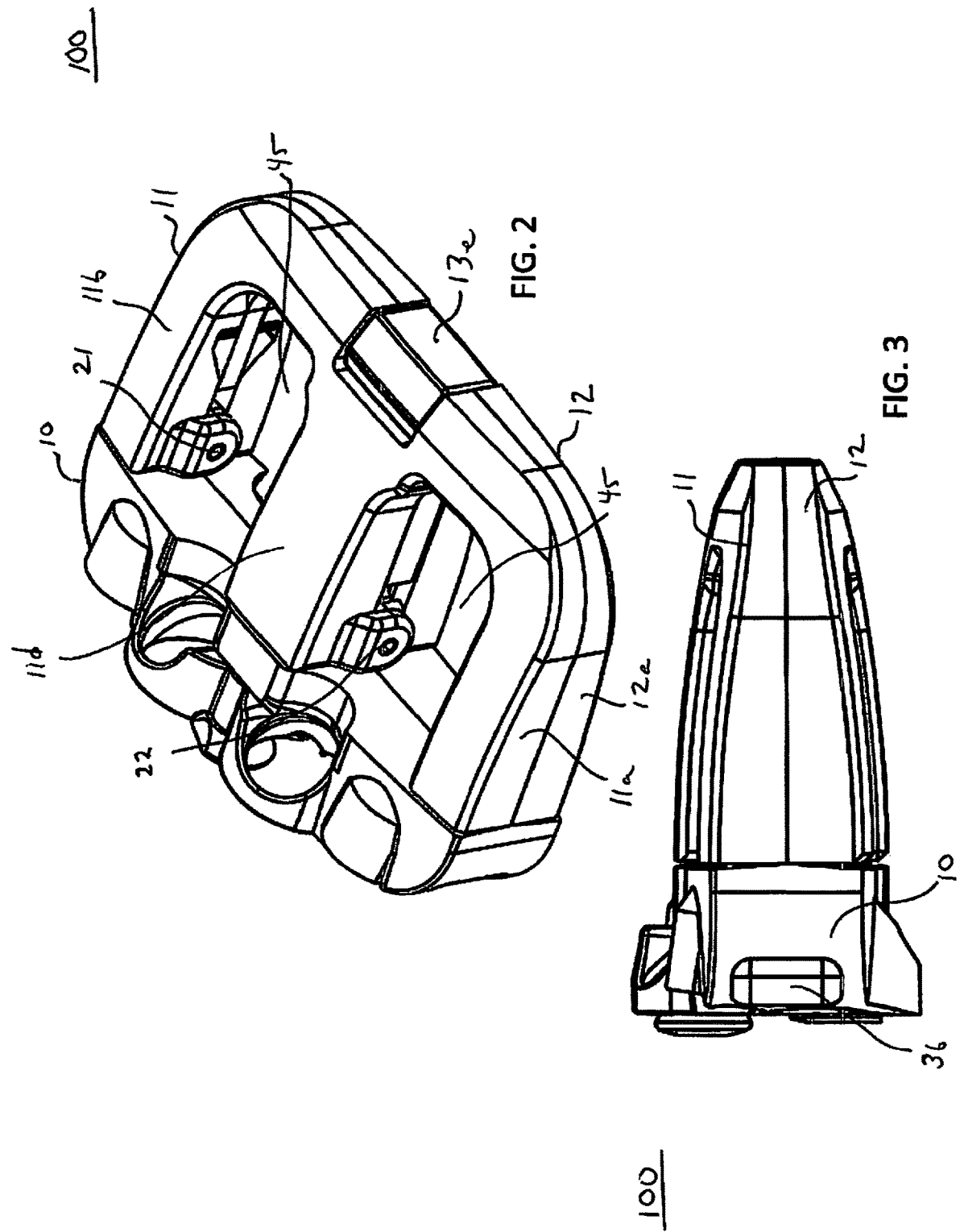

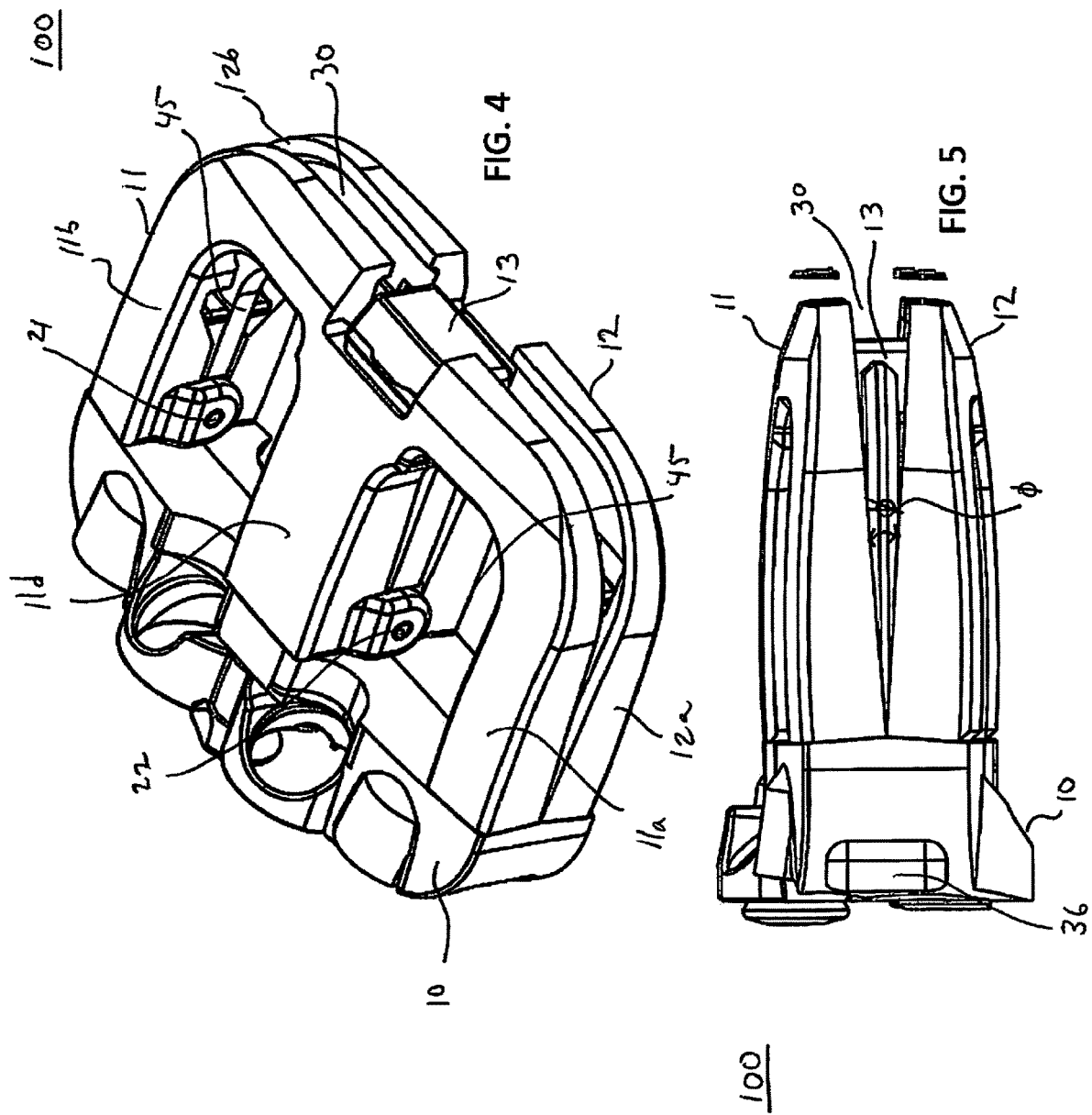

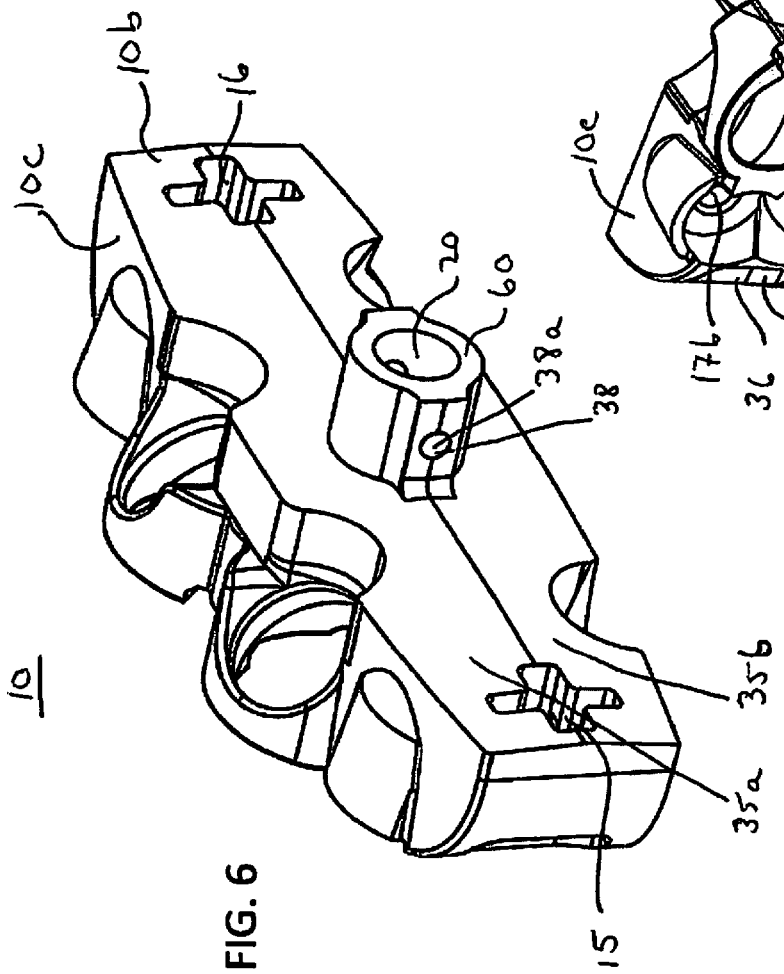
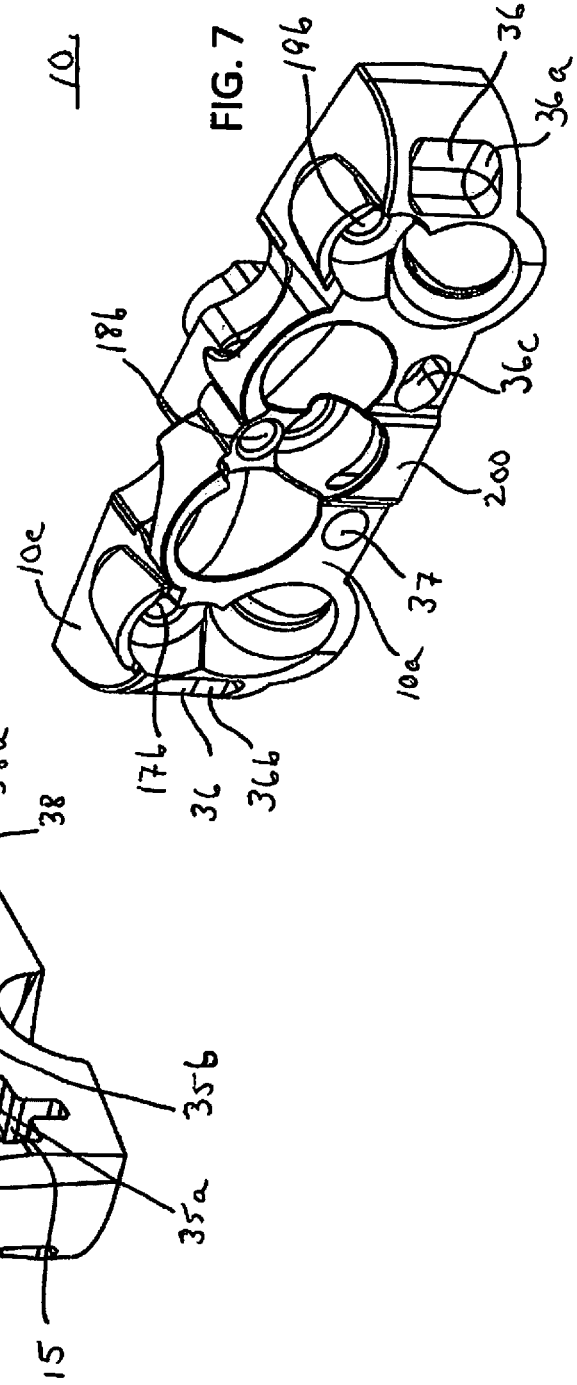
FIG. 6
FIG. 7

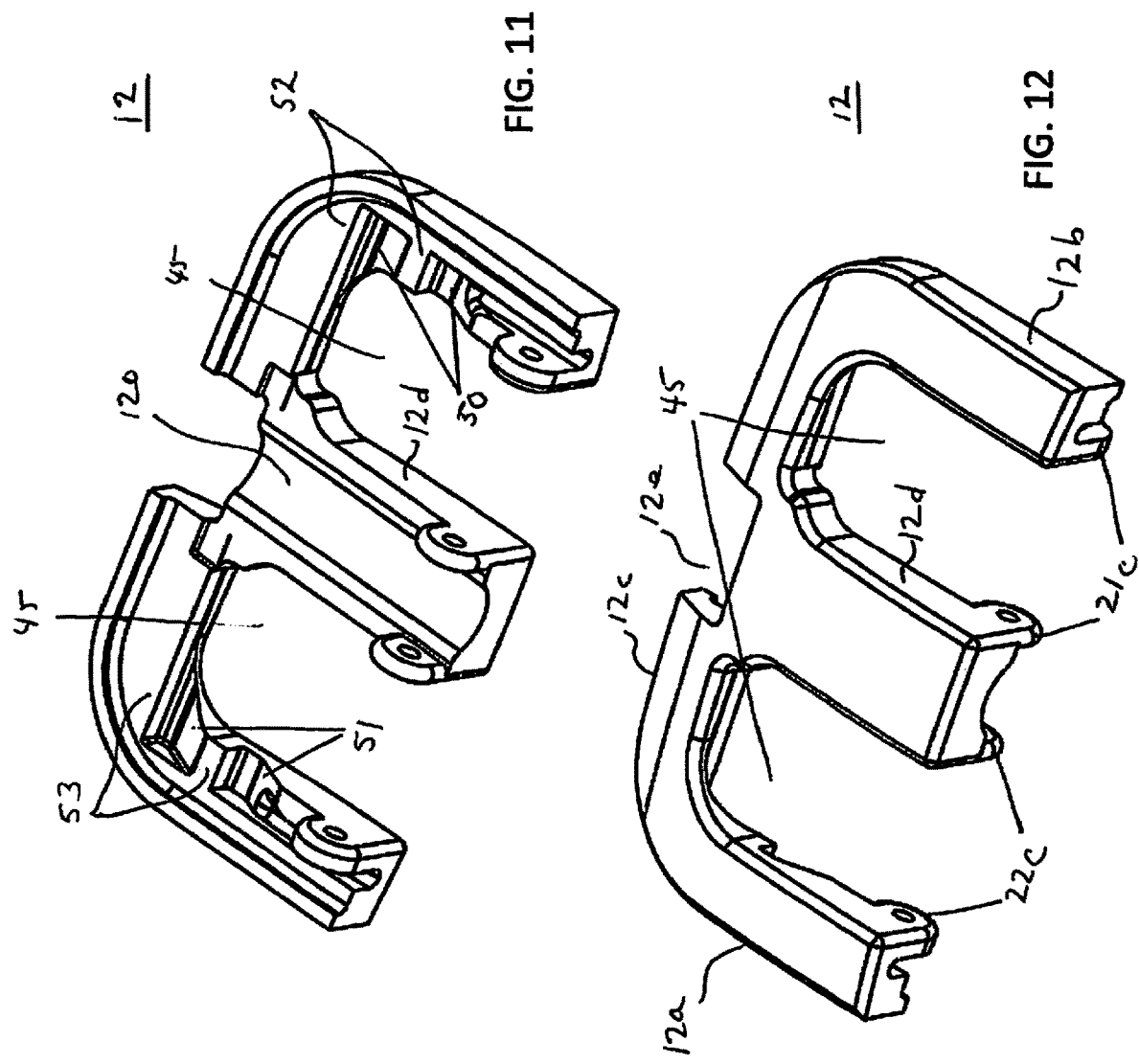

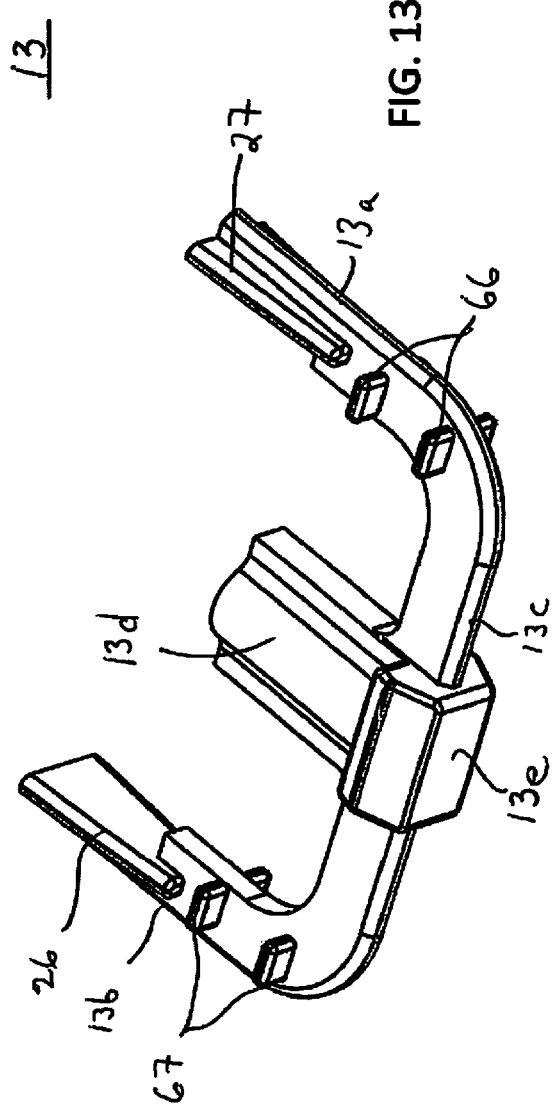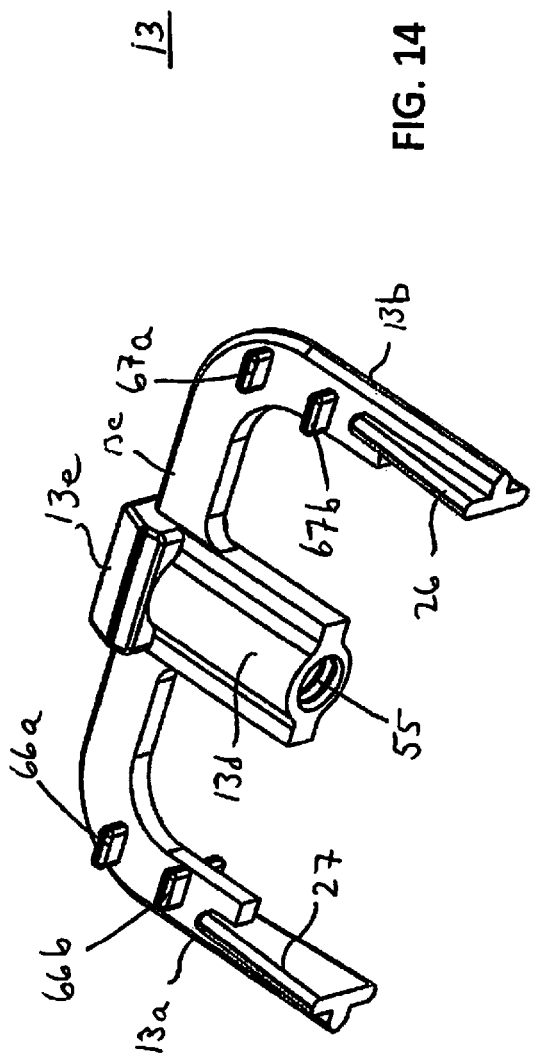

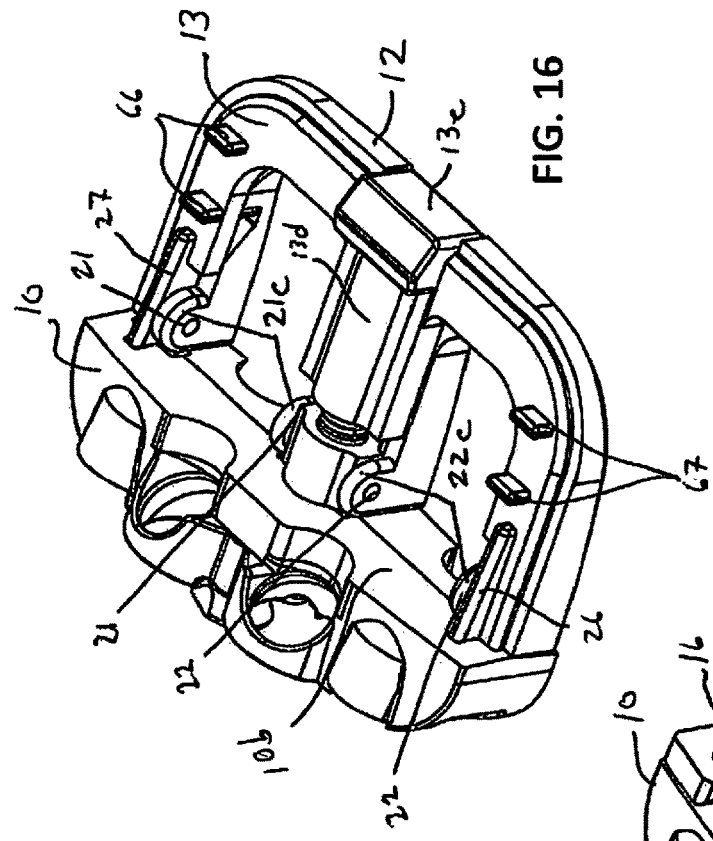
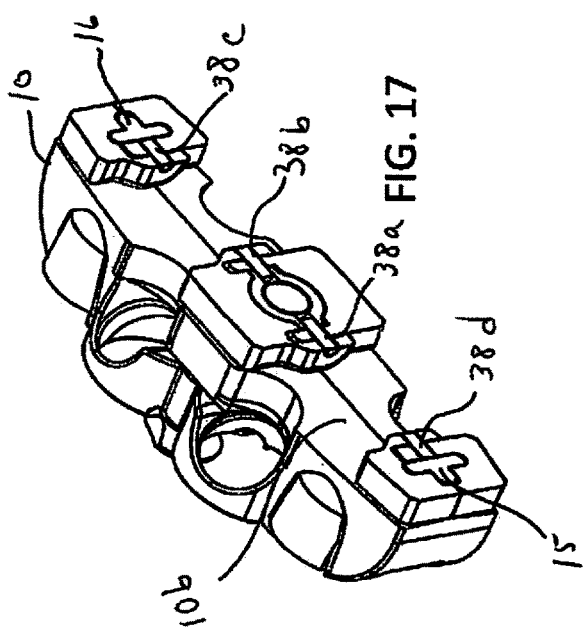

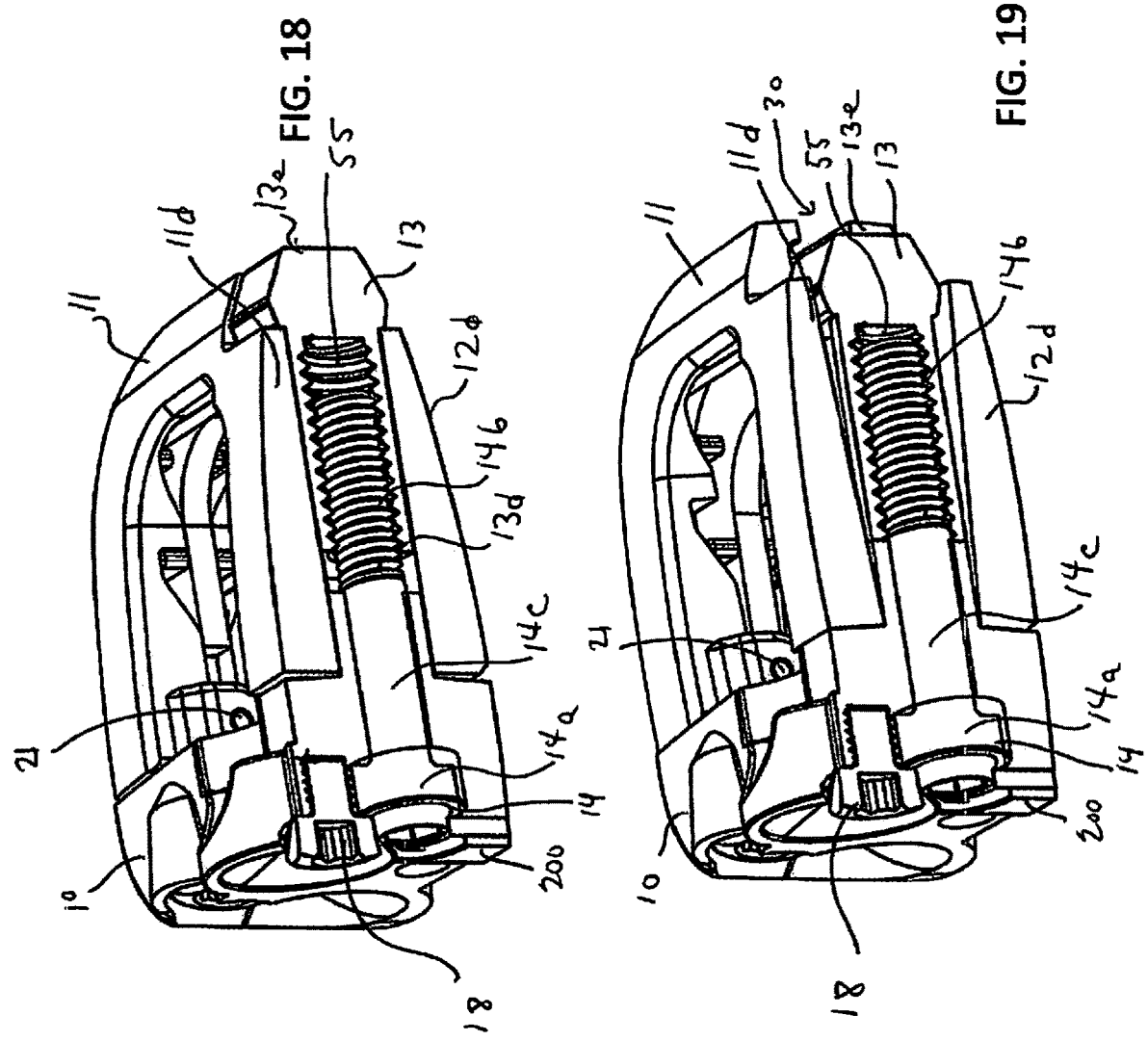

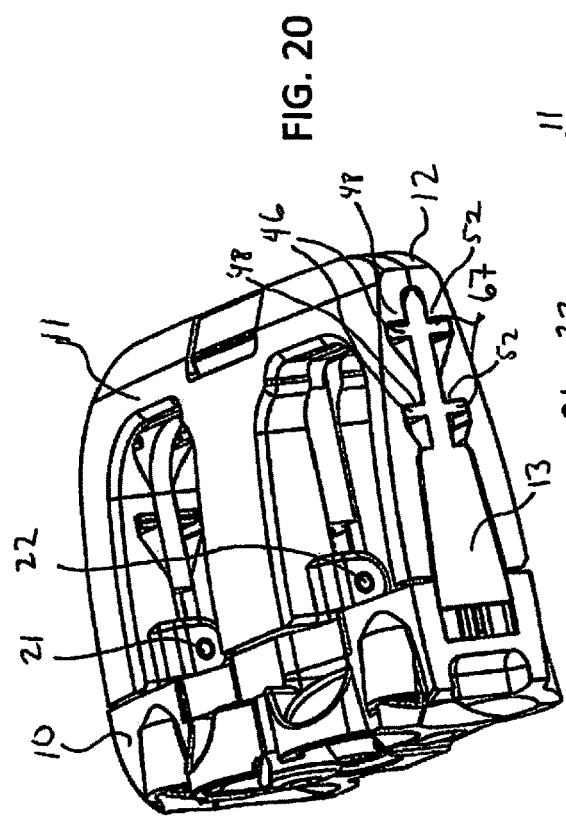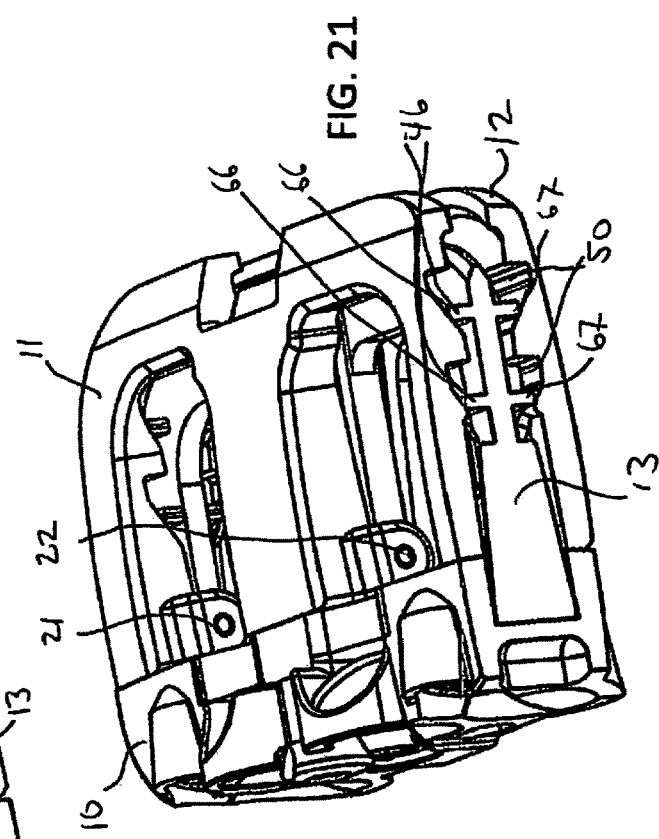

VARIABLE LORDOTIC INTERBODY SPACER

CROSS-REFERENCE TO RELATED APPLICATIONS

The present application is a divisional application of patent application Ser. No. 15/817,793 which is a continuation application of U.S. patent application Ser. No. 14/741,939 filed on Jun. 17, 2015, which is incorporated in its entirety.

FIELD OF THE INVENTION

The present invention relates to intervertebral disc prostheses, and more particularly to a lordotic interbody spacer that is adjusted or expanded in situ to occupy desired space between vertebral bodies.

DESCRIPTION OF THE RELATED ART

Spinal fusion is a surgical technique used to facilitate the growth of bone between two vertebrae. The procedure involves implanting a spacer, such as an interbody device, for example, packed with grafting material into the disc space to stabilize the spine while bone grows in between two vertebrae. As the bone graft material heals, one long bone is formed with the adjacent vertebrae. The purpose is to eliminate movement between the vertebrae to reduce pain and nerve irritation.

An interbody fusion may involve removing the intervertebral disk. When the disk space has been cleared, the interbody device is implanted between the two adjoining vertebrae. These devices may contain the bone graft material that promotes bone healing and facilitates the fusion. After insertion, surgeons may use (e.g., bone) screws, plates, and rods to further stabilize the spine. Interbody fusion can be performed using a variety of different approaches, and, in an anterior lumbar interbody fusion, the procedure is performed from the front of the patient.

Lordotic angle is the angle between the top (superior surface) of the second lumbar vertebra and the bottom (inferior surface) of the fifth lumbar vertebra, used as a measurement of the curve of the lumbar spine. In some instances, it might be desirable to adjust or otherwise set the lordotic angle during the spinal fusion operation to adjust lordosis of the spine.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention enables a spinal fusion treatment with a variable lordotic interbody spacer including: a face plate, superior and inferior endplates, an actuation frame, and an actuation screw. The face plate includes a front surface and a rear surface, the face plate further having at least one actuation channel and at least two stabilizer channels formed through the face plate from the front surface to the rear surface. Each of the superior and inferior endplates has first and second endplate arms coupled by a base in a generally U-shaped configuration, each endplate arm coupled to the rear surface of the face plate via a hinge opposite from the base. Each endplate arm includes a ramp recess on a top surface and on a bottom surface. The actuation frame is positioned between the superior endplate and the inferior endplate, the actuation frame having first and second frame arms coupled by a frame base in a generally U-shaped configuration, each actuation frame arm having a stabilizer feature opposite from the frame base and configured to pass through a corresponding stabilizer channel, the actuation frame further including a receptacle formed at the inside of the frame base. Each frame arm includes an actuation ramp pin on a top surface and on a bottom surface fitted to a corresponding ramp recess. The actuation screw includes a head, body and threaded end, the actuation screw body passing through the actuation channel, the head retained at the front surface and the threaded end threadably coupled to the receptacle of the actuation frame. When operated, the actuation screw moves the actuation frame between the superior endplate and the inferior endplate to adjust an angle there between.

According to another embodiment, a method of treatment includes inserting or implanting the variable lordotic interbody spacer in a disc space between adjacent vertebrae. The variable lordotic interbody spacer may be inserted in a collapsed or closed position, for example. Once implanted into the disc space and seated at the appropriate position, the variable lordotic interbody spacer may be moved or enlarged to an expanded or open position. In particular, the position of the variable lordotic interbody spacer may be expanded to adjust the position of a patient's lordosis via adjustment of the lordotic angle in situ during an interbody fusion operation. It is contemplated that one or more than one variable lordotic interbody spacers or other fusion devices can be inserted in the intervertebral space. It is further contemplated that each variable lordotic interbody spacer does not have to be finally installed in the fully expanded state. Rather, depending on the location of the variable lordotic interbody spacer in the intervertebral disc space, the height of the variable lordotic interbody spacer may vary from unexpanded to fully expanded.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 2 shows a top perspective rear view of the variable lordotic interbody spacer of FIG. 1 in a collapsed position;

FIG. 3 shows a right side view of the variable lordotic interbody spacer of FIG. 1 in the collapsed position;

FIG. 4 shows a top perspective rear view of a variable lordotic interbody spacer of FIG. 1 in an open or expanded position;

FIG. 5 shows a right side of the variable lordotic interbody spacer of FIG. 1 in the open or expanded position;

FIG. 6 shows a rear view of the rear face of the face plate of the variable lordotic interbody spacer of FIG. 1;

FIG. 7 shows a front view of the front face of the face plate of the variable lordotic interbody spacer of FIG. 1;

FIG. 11 shows a bottom view of the inferior endplate of the variable lordotic interbody spacer of FIG. 1;

FIG. 12 shows a top view of the inferior endplate of the variable lordotic interbody spacer of FIG. 1;

FIG. 13 shows a top front view of the actuation frame of the variable lordotic interbody spacer of FIG. 1;

FIG. 14 shows a bottom rear view of the actuation frame of the variable lordotic interbody spacer of FIG. 1;

FIG. 16 shows another perspective view of a subassembly formed of the face plate, inferior endplate and the actuation frame of the variable lordotic interbody spacer of FIG. 1;

FIG. 17 shows a retaining hinge interface of the rear face of the face plate of the variable lordotic interbody spacer of FIG. 1;

FIG. 18 shows a center-line axis, cutaway right side view of the variable lordotic interbody spacer of FIG. 1 showing the operation of the actuation screw to the collapsed position;

FIG. 19 shows a center-line axis, cutaway right side view of the variable lordotic interbody spacer of FIG. 1 showing the operation of the actuation screw to the open position;

FIG. 20 shows a right-side arm, cutaway right side view of the variable lordotic interbody spacer of FIG. 1 showing the operation of the actuation screw to the collapsed position;

FIG. 21 shows a right-side arm, cutaway right side view of the variable lordotic interbody spacer of FIG. 1 showing the operation of the actuation screw to the open position.

DETAILED DESCRIPTION

In accordance with the described embodiments, a variable lordotic interbody spacer includes: a face plate, superior and inferior endplates coupled to the face plate via a hinge, an actuation frame between the endplates, and an actuation screw. The face plate includes actuation and stabilizer channels. Each of the endplates has endplate arms coupled by an endplate base, and includes actuation ramp recesses. The actuation frame includes frame arms coupled by a frame base in a generally U-shaped configuration, each actuation frame arm having a stabilizer feature passing through a corresponding stabilizer channel and having actuation ramp pins fitted to a corresponding ramp recesses. The actuation screw passes through the actuation channel, with a head retained at the front surface and a threaded end coupled to the actuation frame. When operated, the actuation screw moves the actuation frame between the superior endplate and the inferior endplate to adjust an angle there between. A variable lordotic interbody spacer in accordance with the described embodiments might allow for a surgeon to adjust the position of a patient's lordosis via adjustment of the lordotic angle in situ during an interbody fusion operation.

Figure 1:
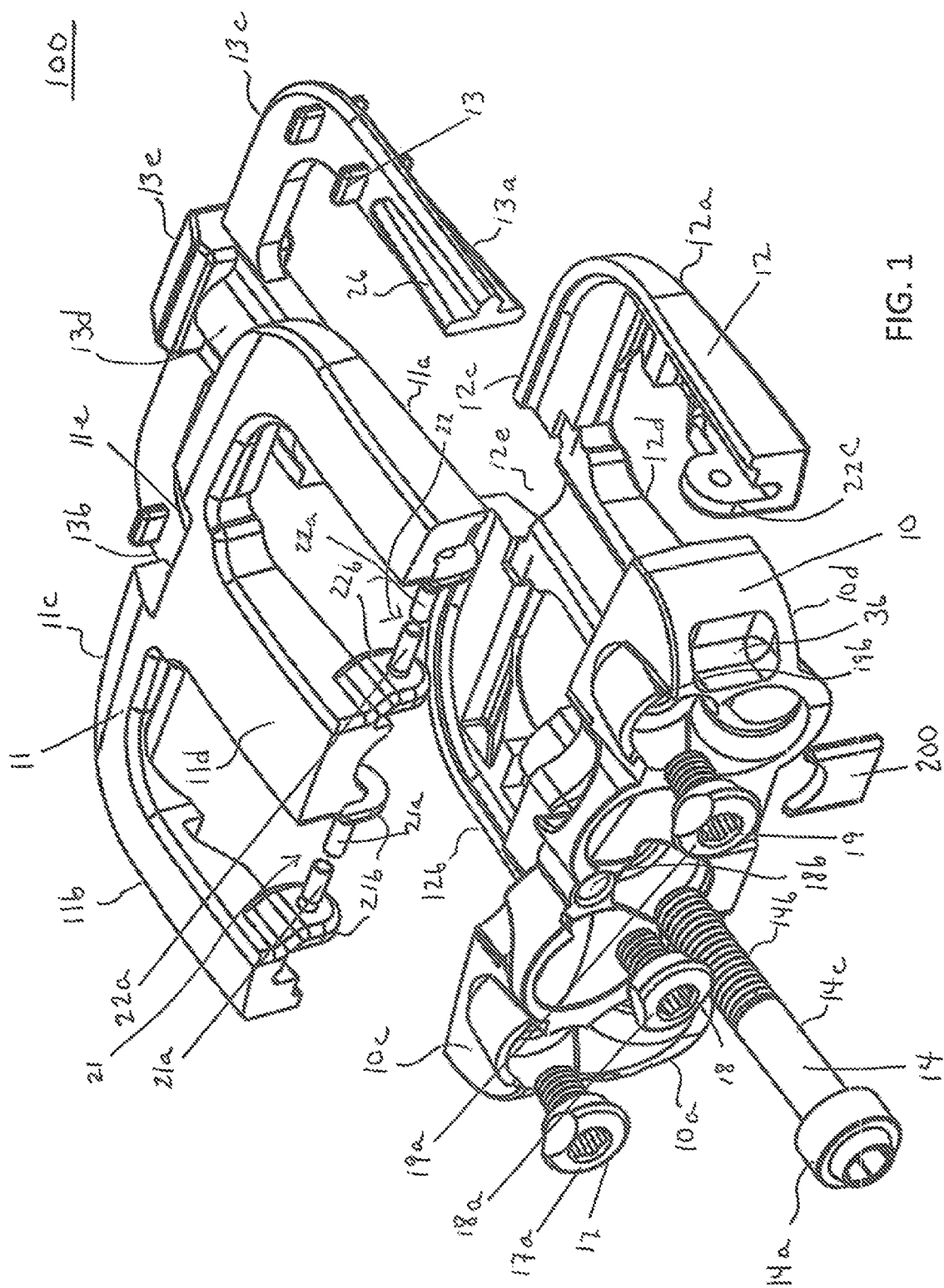
FIG. 1 shows an exploded top front view of a variable lordotic interbody spacer with separated elements including a face plate, superior and inferior endplates, actuation frame and actuation screw in accordance with one embodiment.

FIG. 1 shows an exploded perspective top front view of a variable lordotic interbody spacer 100 with separated elements including face plate 10, superior endplate 11, inferior endplate 12, actuation frame 13, and actuation screw 14 in accordance with an exemplary embodiment of the present invention. Face plate 10 includes front face 10a, rear face 10b, top 10c and bottom 10d. As used herein, the term "face" generally refers to a particular surface that may have one or more features thereon. Superior endplate 11 includes first arm 11a, second arm 11b, generally U-shaped base 11c, center housing 11d, and recess 11e formed at the center of base 11c. Inferior endplate 12 includes first arm 12a, second arm 12b, generally U-shaped base 12c, center housing 12d, and recess 12e formed at the center of base 12c.

Actuation frame 13 includes first arm 13a, second arm 13b, generally U-shaped base 13c, center core 13d, and knob 13e formed at the center of base 13c. Knob 13e formed at the center of base 13c might be configured so as to fit in recesses 11e and 12e, as shown in the figures. Knob 13e might be configured so as to fit in recesses 11e and 12e to guide actuation frame 13 between superior endplate 11 and inferior endplate 12 to prevent sideways movement under force, as well as to start to force superior endplate 11 and inferior endplate 12 apart when actuation screw 14 is operated, as described subsequently. Actuation screw 14 includes head 14a, bottom, threaded end 14b, and body section 14c. Actuation screw 14 is retained in face plate 10 by screw plate retainer 200 fastened to front face 10a.

Lordotic interbody spacer 100 includes blocking assemblies 17, 18 and 19 comprising blocking screw screws 17a, 18a, and 19a that might be threadably inserted into corresponding blocking screw channels 17b, 18b and 19b, as described subsequently.

Superior endplate 11 and inferior endplate 12 are coupled to rear face 10b of face plate 10 via hinges 21 and 22, Hinge 21 includes pins 21a coupling ears 21b and 21c of superior endplate 11 and inferior endplate 12, respectively. Similarly, hinge 22 includes pins 22a, and coupling ears 22b and 22c of superior endplate 11 and inferior endplate 12, respectively.

FIG. 2 shows a perspective top rear view of variable lordotic interbody spacer 100 of FIG. 1 in a collapsed position. FIG. 3 shows a right side of the variable lordotic interbody spacer 100 of FIG. 1 in the collapsed position in accordance with an exemplary embodiment. As is evident, the superior endplate 11 and inferior endplate 12 are substantially in contact with one another. In particular, knob 13e is sized and configured to fit in at least a portion of recesses 11e and 12e in the superior and inferior endplates 11, 12 such that the superior and inferior endplates 11, 12 have a minimum height. The knob 13e may be substantially flush with an outermost end of the superior and inferior endplates 11, 12. In addition, the end of the superior and inferior endplates 11, 12 designed to enter into the disc space may include at least one angled surface, which serve to distract the adjacent vertebral bodies when the spacer 100 is inserted into the intervertebral space. As best seen in FIG. 3, there may be at least two opposing angled surfaces forming a generally wedge shape to distract the adjacent vertebral bodies when the spacer 100 is inserted into the intervertebral space.

FIG. 4 shows a perspective top rear view of the variable lordotic interbody spacer 100 of FIG. 1 in an open or expanded position. As shown in FIG. 4 and compared to FIGS. 2 and 3, in an open or fully expanded position, actuation frame 13 is moved toward the rear face 10a of face plate 10, separating superior endplate 11 and inferior endplate 12. When in the open position, a gap 30 is formed between superior endplate 11 and inferior endplate 12. FIG. 5 shows a right side of the variable lordotic interbody spacer 100 of FIG. 1 in the open or fully expanded position. As shown in FIG. 5, when in the open position, gap 30 formed between superior endplate 11 and inferior endplate 12 creates an angle ϕ between superior endplate 11 and inferior endplate 12. As such the upper and lower contact surfaces of the superior and inferior endplates 11, 12, respectively, do not maintain a parallel configuration. Instead, the upper and lower contact surfaces of the superior and inferior endplates 11, 12 are angled to align with corresponding patient anatomy. Consequently, angle ϕ between superior endplate 11 and inferior endplate 12 allows for a surgeon to adjust the position of a patient's lordosis via adjustment of the lordotic angle. As the actuation frame 13 is drawn back, the angle ϕ between superior endplate 11 and inferior endplate 12 increases. In other words, as the actuation frame 13 insets a distance from the end of the spacer 100, the angle ϕ between superior endplate 11 and inferior endplate 12 increases causing a greater degree of separation between the ends of the superior and inferior endplates 12 and a greater angle ϕ and larger gap 30. Although shown in FIGS. 4 and 5 in a fully expanded configuration with a maximum angle ϕ, it is contemplated that the spacer 100 does not have to actuated to the fully expanded state. Rather, the height of the spacer 100, the angle ϕ, and the gap 30 may be optimized to any suitable position from the fully collapsed to fully expanded positions and anywhere in between.

FIG. 6 shows a perspective view of the rear face 10b of face plate 10 of FIG. 1. Rear face 10b includes stabilizer channels 15 and 16, and actuation channel 20. Stabilizer channels 15 and 16 are sized and configured to receive first arm 13a and second arm 13b, respectively, of actuation frame 13. Stabilizer channels 15 and 16, first arm 13a, and second arm 13b are generally configured so as to be keyed, thereby guiding and preventing rotational movement of first arm 13a and second arm 13b when subject to force. In particular, as shown in FIG. 6, stabilizer channels 15 and 16 may be provided with a substantially plus-shaped recess, which are sized and configured to receive a corresponding t-shaped extension on arms 13a, 13b of the actuation frame 13. The other portion of the plus-shaped recess may receive pins 21a and 22a (best seen in the exploded view in FIG. 1), respectively. Preferably, the stabilizer channels 15 and 16 and corresponding extensions on arms 13a, 13b permit movement of the actuation frame during expansion and contraction of the spacer 100.

Also as shown in FIG. 6, actuation channel 20 passes through face plate 10 and may extend through protrusion 60. Protrusion 60 is shown having holes 38 (hole 38a shown, with hole 38b, not shown, on opposite side of protrusion 60) to receive retaining pins 21a and 22a of hinges 21 and 22, thereby coupling superior endplate 11 and inferior endplate 12 to rear face 10b of face plate 10. Rear face 10b might be configured with upper and lower tapered walls 35a and 35b, respectively, to provide clearance for hinges 21 and 22.

FIG. 7 shows a perspective view of the front face 10a of the face plate 10 of variable lordotic interbody spacer 100 of FIG. 1. In order for a user to hold variable lordotic interbody spacer 100 with a tool (not shown in the figures), face plate 10 might be provided with one or more keyed holes 36, shown as holes 36a, 36b, and 36c, and tapped hole 37. Keyed holes 36a, 36b, and 36c are keyed to corresponding features of the tool so as to hold spacer 100 without movement and keep variable lordotic interbody spacer 100 steady. Tapped hole 37 may be provided to allow a corresponding threaded or tapered element of the tool to be fixed to front face 10a of the variable lordotic interbody spacer 100.

Figure 8:
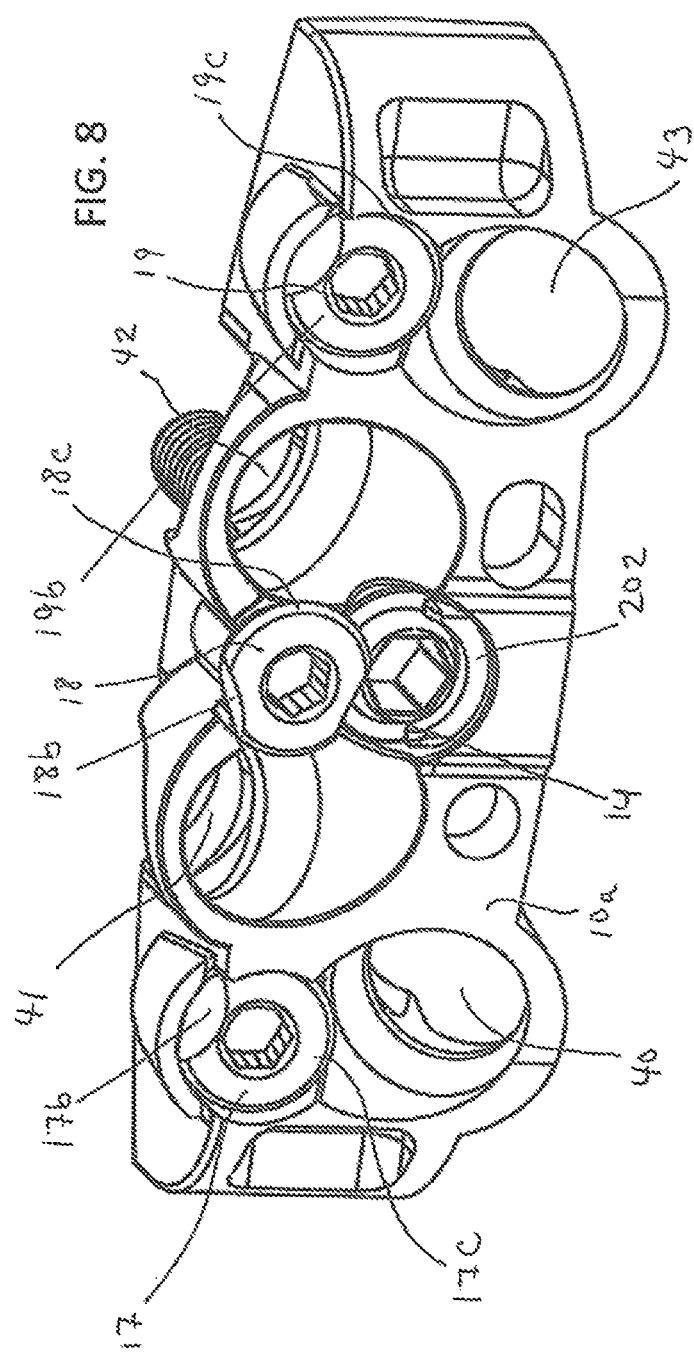
FIG. 8 shows the blocking screws, the actuation screw, and the screw retainer plate as positioned in the front face of the face plate of the variable lordotic interbody spacer of FIG. 1.

FIG. 8 shows blocking screw assemblies 17, 18 and 19 including corresponding blocking screws 17a, 18a and 19a, and blocking screw channels 17b, 18b and 19b as positioned in front face 10a of face plate 10 of variable lordotic interbody spacer 100. FIG. 8 also shows bone screw channels 40, 41, 42, and 43 which allow passage of bone screws through variable lordotic interbody spacer 100 to fix spacer 100 to a patient's vertebrae (spine). Projections or eyebrows in top 10c and bottom 10d of the face plate 10 may be provided. The bone screw channels 40, 41, 42, and 43 may be provided at an angle to allow for the bone screws to be secured to adjacent upper and lower vertebrae, respectively, and to provide for maximum screw purchase into the vertebrae. The bone screws may be any suitable screws known in the art including fixed or variable angle. As shown, when blocking screws 17a, 18a and 19a are inserted to full depth in blocking screw channels 17b, 18c and 19d, blocking screw heads 17c, 18c and 19c cover a portion of bone screw channels 40, 41, 42, and 43, allowing for retention of bone screws in bone screw channels 40, 41, 42, and 43 (e.g., to prevent bone screws from working themselves out of variable lordotic interbody spacer 100).

Figure 9:
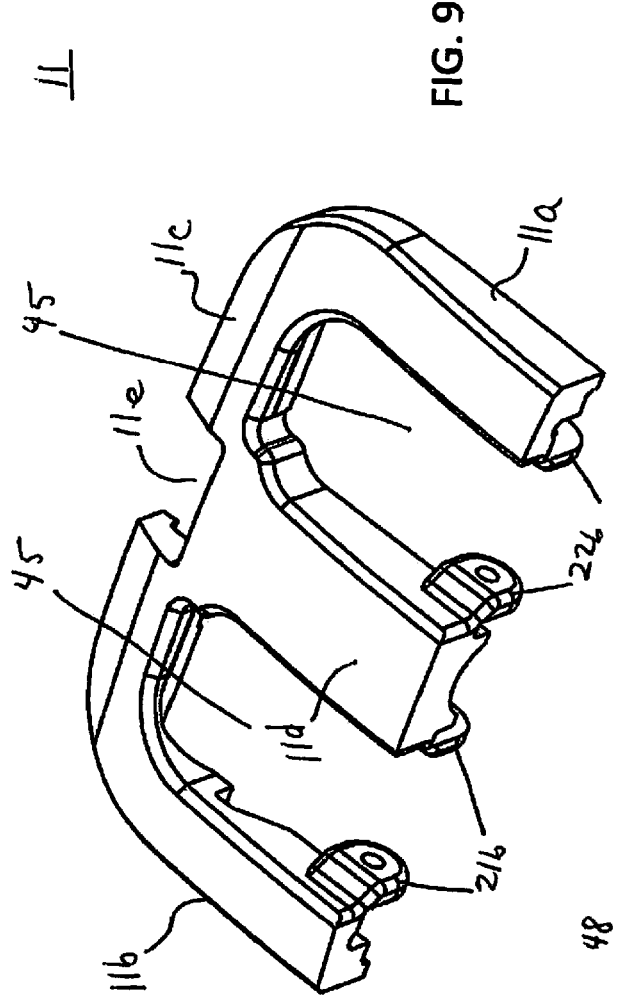
FIG. 9 shows a top view of the superior endplate of the variable lordotic interbody spacer of FIG. 1.

FIG. 9 shows a top perspective view of superior endplate 11 of variable lordotic interbody spacer 100 of FIG. 1. As shown in the figure, the volume (cavity) between first arm 11a and center housing 11d, and the volume (cavity) between second arm 11b and center housing 11d, both bounded by base 11c and rear face 10b of face plate 10, form graft window regions 45. Graft window regions 45 allow for insertion of graft material within variable lordotic interbody spacer 100. The window regions 45 may be configured for receiving and retaining one or more bone graft materials to promote fusion of the adjacent vertebral bodies. For example, cadaveric bone, autologous bone, bone slurry, BMP, or other similar materials, may enhance tissue growth within the intervertebral space.

Figure 10:
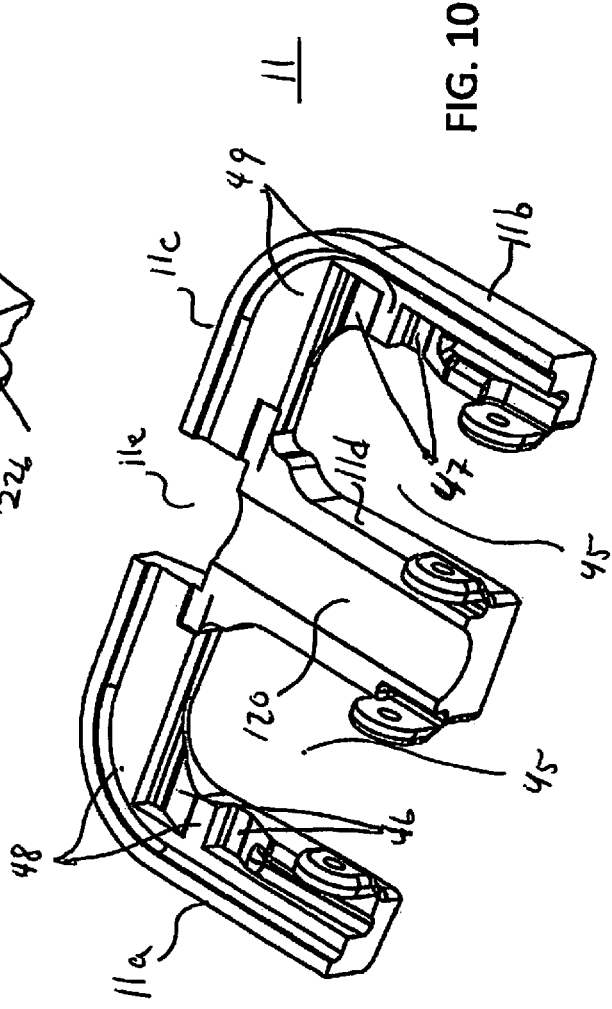
FIG. 10 shows a bottom view of the superior endplate of the variable lordotic interbody spacer of FIG. 1.

FIG. 10 shows a bottom of superior endplate 11 of variable lordotic interbody spacer 100 of FIG. 1 including actuation ramp recesses 46 and 47. While FIG. 10 is described having two ramp recess areas per arm surface, the invention is not limited and one skilled in the art might employ more or less ramp recess areas per arm surface. Each ramp recess area of actuation ramp recesses 46 and 47 includes a ramp at its bottom, with each ramp recess area becoming shallower toward the ends of arms 11a and 11b coupled to rear face 10b of face plate 10 (not shown in FIG. 10) and deeper toward base 11c. Each ramp recess area of actuation ramp recesses 46 and 47 is bounded by a corresponding wall stop (wall stops 48 and 49) formed within first arm 11a and second arm 11b toward base 11c. Also shown in FIG. 10, center housing 11d includes a hollowed area on the bottom forming half of actuation screw receptacle channel 120, described subsequently.

FIG. 11 shows a perspective bottom view of inferior endplate 12 of variable lordotic interbody spacer 100. Inferior endplate 12 includes actuation ramp recesses 50 and 51 with corresponding stop walls 52 and 53, respectively. FIG. 12 shows a top of inferior endplate 12 of variable lordotic interbody spacer 100 of FIG. 1, and shows graft window regions 45 for graft material. Top and bottom of inferior endplate 12 include similar features to, and are similarly configured and formed as, corresponding top and bottom of superior endplate 11, so further detailed description is omitted herein.

FIG. 13 shows a top rear surface of actuation frame 13 of variable lordotic interbody spacer 100 of FIG. 1. As shown, the top surface includes stabilizers 26 and 27, and actuation ramp pins 66 and 67. In particular, each of stabilizers 26 and 27 is formed by a vertical protrusion on the top surface of actuation frame 13 along the axis of and at the corresponding ends toward face plate 10 of first arm 13a and second arm 13b, respectively, and is keyed with the corresponding stabilizer channel within face plate 10, as described previously. The vertical protrusion of each stabilizer 26 and 27 may be tapered along the corresponding arm depending on the embodiment. In particular, the stabilizers 26 and 27 may have a greatest height at the outermost end of arms 13a and 13b of the frame 13 and narrowest at a distance along arms 13a and 13b. The ramped protrusions of stabilizers 26 and 27 may extend along a portion of the distance of arms 13a and 13b (e.g., about half way) or the entire distance of the frame 13.

Further, FIG. 13 shows actuation ramp pins 66 and 67, which are discrete vertical protrusions on the top surface of actuation frame 13 perpendicular to the axis of and at the corresponding ends toward base 13c of first arm 13a and second arm 13b. Actuation ramp pins 66 and 67 are positioned on the top surface of actuation frame 13 so as to fit and move within corresponding actuation ramp recesses 46 and 47. Actuation ramp pins 66 and 67 each comprise two separate pins, shown as 66a and 66b, and 67a and 67b, respectively, though one skilled in the art might extend the teachings herein to employ a single actuation ramp pin, or three or more actuation ramp pins, depending on the embodiment.

FIG. 14 shows a bottom view of actuation frame 13, which bottom surface also includes stabilizers 26 and 27 and actuation ramp pins 66 and 67. The actuation frame 13 also includes actuation screw receptacle 13d formed at the interior of base 13c and opposite to knob 13e. Actuation screw receptacle 13d includes threaded hole 55 sized and configured to receive threaded base 14b of actuation screw 14 (not shown in FIG. 14). The outer surface of actuation screw receptacle 13d may be formed in a shape to move in a restricted manner within actuation screw receptacle channel 120 formed by hollowed areas of center housings 11d and 12d (not shown in FIG. 14).

Since the opposite, bottom front and rear surfaces of actuation frame 13 include similar features to, and are similarly configured and formed as, corresponding top front and rear surfaces of actuation frame 13 shown in FIG. 13, detailed description of the bottom front and rear surfaces of actuation frame 13 is omitted herein.

Figure 15:
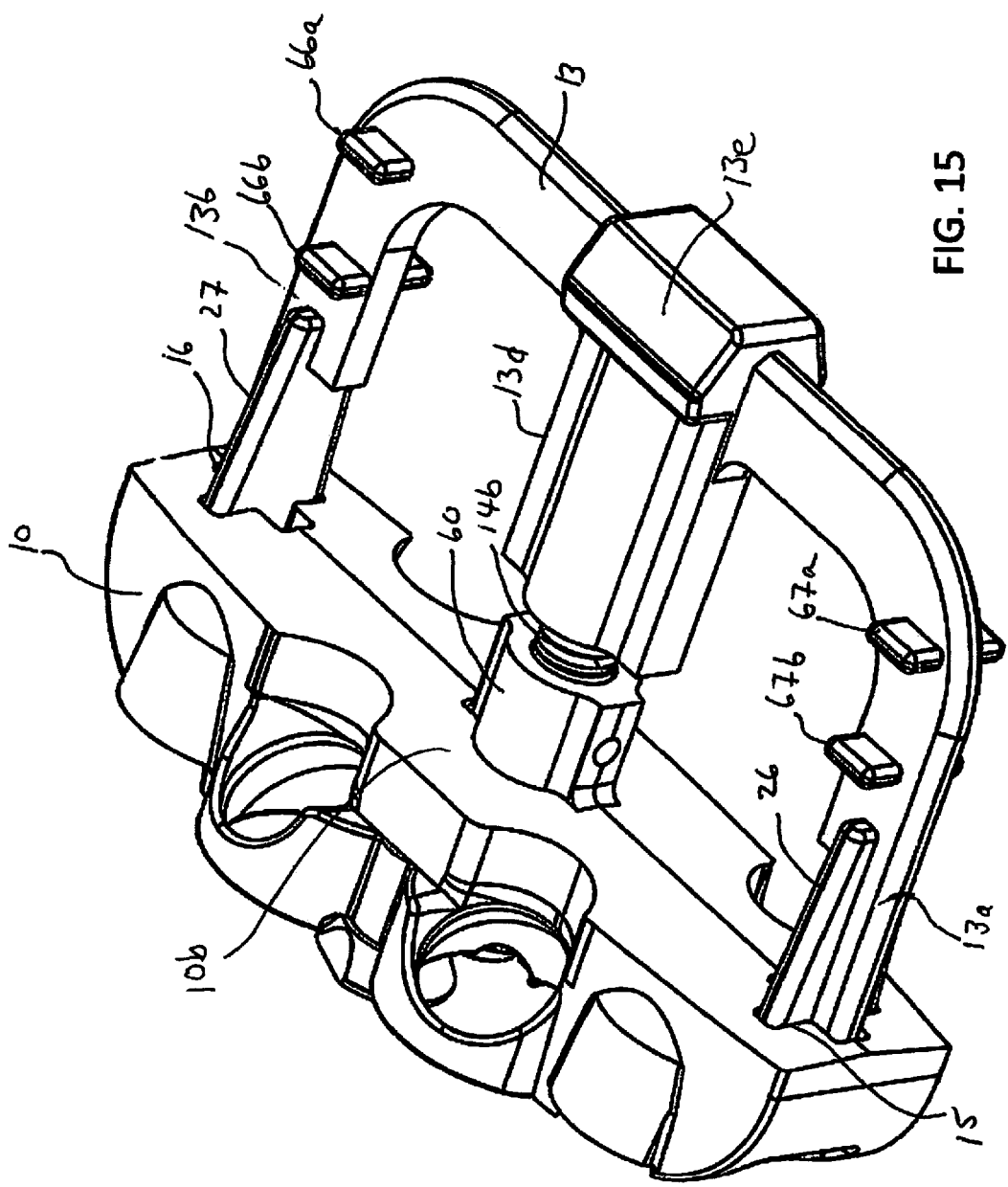
FIG. 15 shows a perspective view of a subassembly formed of the face plate and the actuation frame of the variable lordotic interbody spacer of FIG. 1.

FIGS. 15, 16 and 17 show additional detail of the spacer 100. FIG. 15 shows a subassembly formed of face plate 10 and actuation frame 13 and illustrates the coupling of face plate 10 to actuation frame 13 via threaded end 14b of actuation screw 14, as well as the insertion of stabilizers 26 and 27 into corresponding stabilizer channels 15 and 16, respectively. FIG. 16 shows detail on the formation of hinges 21 and 22 on rear face 10b of face plate 10 of the variable lordotic interbody spacer 100. In particular, FIG. 16 shows the subassembly of FIG. 15 formed with the added inferior endplate 12, showing tabs 21c and 22c fastened into the hinges 21 and 22 by pins 21a and 22a, respectively. FIG. 17 shows a retaining hinge interface of rear face 10b of face plate 10 showing pin recesses 38a-38d for receiving pins 21a and 22a (best seen in the exploded view in FIG. 1), respectively.

Operation of the variable lordotic interbody spacer 100 of FIG. 1 is now described with respect to FIGS. 18 through 21.

FIG. 18 shows a center-line axis, cutaway right side view of the variable lordotic interbody spacer 100 showing the operation of actuation screw 14, with the spacer 100 in the collapsed position. Starting in the collapsed position, as actuation screw 14 is rotated clockwise, threaded end 14b rotates in threaded hole 55 of actuation screw receptacle 13d. Since head 14a is retained by screw retainer plate 200, actuation screw 14 does not change position relative to face plate 10 other than to rotate, which exerts a pulling force on actuation screw receptacle 13d. Consequently, actuation frame 13 is drawn back toward face plate 10, forcing superior endplate 11 and inferior endplate 12 apart. Superior endplate 11 and inferior endplate 12 are coupled to rear face 10b of face plate 10 via hinges 21 and 22, so these arm endpoints do not move, but rather rotate about the hinge pins.

FIG. 19 shows a center-line axis, cutaway right side of the variable lordotic interbody spacer 100 showing the operation of the actuation screw 14 to move the spacer 100 to the open or expanded position. Consequently, in the open position shown in FIG. 19, the gap 30 is formed at respective bases between superior endplate 11 and inferior endplate 12, creating the angle φ between superior endplate 11 and inferior endplate 12 (shown in FIG. 5). As shown in FIG. 19, the knob 13e of the frame 13 is inset into the body of the spacer 100. As the actuation screw 14 is rotated, the actuation frame 13 is drawn toward the face plate 10, the angle φ between superior endplate 11 and inferior endplate 12 becomes larger and the gap 30 increases to create a greater angle between the superior endplate 11 and inferior endplate 12.

FIG. 20 shows a right-side arm, cutaway right side of the variable lordotic interbody spacer 100 showing actuation screw 14 in the collapsed position, and FIG. 21 shows the right-side arm, cutaway right side of the variable lordotic interbody spacer 100 showing the operation of actuation screw 14 to the open or expanded position. Initially, as seen in FIG. 20, endplates 11 and 12 are closed as action ramp pins 46 are at the bottom of ramp recesses 67 against wall stops 48 and 52. As actuation screw 14 is rotated in a first direction (e.g., clockwise), endplates 11 and 12 are forced open as action ramp pins 46 ride up the ramps at the bottom of ramp recesses 46 and 50. As a result, the superior endplate 11 and inferior endplate 12 are separated from one another as shown in FIG. 21.

Figure 22:
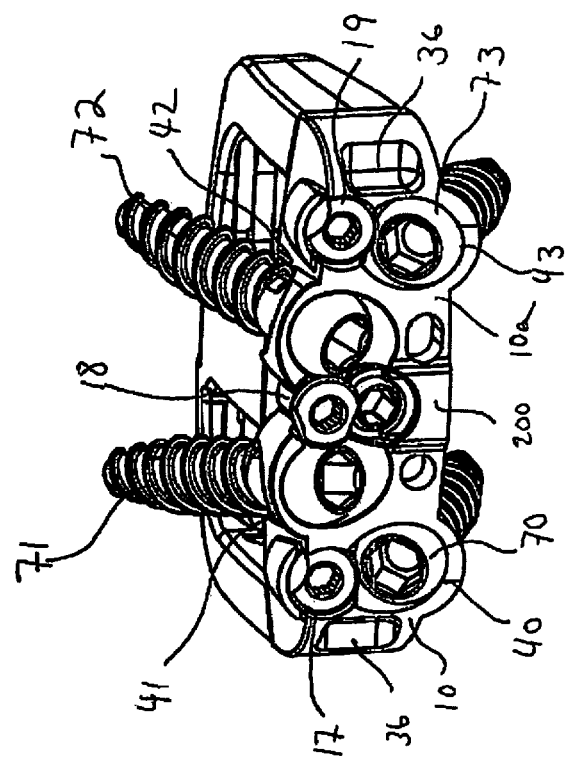
FIG. 22 shows a perspective view of the front face of the face plate including bone screws of the variable lordotic interbody spacer of FIG. 1.

FIG. 22 shows the front face 10a of the face plate 10 including bone screws 70, 71, 72 and 73 in corresponding bone screw channels 40, 41, 42 and 43. As shown, blocking screw assemblies 17, 18 and 19 operate to retain bone screws 70, 71, 72 and 73 in corresponding bone screw channels 40, 41, 42 and 43. After the bone screws 70, 71, 72 and 73 have been inserted through the corresponding bone screw channels 40, 41, 42 and 43, the blocking assemblies 17, 18, and 19 can be rotated to block and prevent the bone screw from inadvertently backing out. In particular, blocking screw assembly 17 blocks bone screw 70; blocking screw assembly 18 blocks bone screws 71 and 72; and blocking screw assembly 19 blocks bone screw 73. Thus, the blocking screw assemblies 17, 18, and 19 operate to prevent the respective bone screws 70, 71, 72, and 73 from backing out of the face plate 10 once implanted in the vertebrae. Although not shown, the superior and inferior endplates 11 and 12 may optionally be provided with teeth or other projections which can engage or penetrate body tissue to reduce a likelihood of migration of spacer 100 after implantation. With these features, the spacer 100 can advantageously serve as a standalone spacer without the need for additional fixation.

In accordance with the invention, implants of various sizes may be provided to best fit the anatomy of the patient. The desired degree of expansion may be selected to provide for a natural lordosis, or a corrective lordosis, for example, of from 0° to 6° for a cervical application, or from 3°-16° for a lumbar application, although much different values may be advantageous for other joints. Lordotic angles may also be formed by shaping one or both of endplates 11, 12 to have relatively non-coplanar surfaces. Spacers 100 may be implanted within any level of the spine, and may also be implanted in other joints of the body, including joints of the hand, wrist, elbow, shoulder, hip, knee, ankle, or foot.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Although the subject matter described herein may be described in the context of illustrative implementations to process one or more computing application features/operations for a computing application having user-interactive components the subject matter is not limited to these particular embodiments. Rather, the techniques described herein can be applied to any suitable type of user-interactive component execution management methods, systems, platforms, and/or apparatus.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements.

Further, the term "comprises or includes" and/or "comprising or including" used in the document means that one or more other components, steps, operation and/or existence or addition of elements are not excluded in addition to the described components, steps, operation and/or elements.

No claim element herein is to be construed under the provisions of 35 U.S.C. § 112, sixth paragraph, unless the element is expressly recited using the phrase "means for" or "step for."

It is understood that various changes in the details, materials, and arrangements of the parts which have been described and illustrated in order to explain the nature of this invention may be made by those skilled in the art without departing from the scope of the embodiments of the invention as encompassed in the following claims.

I claim:

1. A method of implanting a variable lordotic interbody spacer in a disc space between two adjacent vertebrae, the method comprising:
   inserting the spacer in the disc space, the spacer comprising:
      a face plate having a front surface and a rear surface, the face plate further having at least one actuation channel;
      superior and inferior endplates, each of the endplates having proximal and distal ends and having first and second endplate arms coupled by an endplate base, each endplate arm coupled to the rear surface of the face plate opposite from the base, and each endplate arm having a ramp recess on a top surface and a bottom surface;
      an actuation frame positioned between the superior endplate and the inferior endplate, the actuation frame having first and second frame arms coupled by a frame base, each frame arm having an actuation ramp pin on a top surface and on a bottom surface fitted to a corresponding ramp recess, the actuation frame further including a receptacle formed at the inside of the frame base between each frame arm; and
      an actuation screw having a head, body and threaded end, the actuation screw body passing through one of the at least one actuation channel, the head retained at the front surface and the threaded end threadably coupled to the receptacle of the actuation frame,
      wherein, when operated, the actuation screw moves the actuation frame between the superior endplate and the inferior endplate causing the superior and inferior endplates to pivot with respect to each other such that the distance between the distal end of the superior and inferior endplates increases and the distance between the proximal ends of superior and inferior endplates remains the same, adjusting an angle formed between the superior and inferior endplates, and wherein the actuation screw is configured to be retained in the face plate by a screw plate retainer fastened to the front surface of the face plate, wherein the screw plate retainer is configured to allow rotation of the actuation screw within the face plate while otherwise preventing the actuation screw from changing position relative to the face plate.

2. The method of claim 1, wherein at least two stabilizer channels are formed in the face plate and configured to receive the first and second frame arms, respectively.

3. The method of claim 1, wherein, when rotated, the actuation screw moves the actuation frame toward the face plate to adjust the angle formed between the superior and inferior endplates.

4. The method of claim 1, further comprising at least one blocking assembly formed on the front surface of the face plate, each blocking assembly comprising a blocking screw and a blocking screw channel, wherein the blocking assembly allows for threaded insertion of the blocking screw into the corresponding blocking screw channel.

5. The method of claim 4, wherein one blocking assembly is located adjacent to the head of the actuation screw, wherein, when tightened, the blocking screw of the one blocking assembly prevents the operation of the actuation screw.

6. The method of claim 4, further comprising at least one bone screw channel formed through the face plate between the front and rear surfaces, wherein one blocking assembly is located adjacent to a corresponding bone screw channel, and wherein, when tightened, the blocking screw of the one blocking assembly retains a bone screw in the corresponding bone screw channel.

7. The method of claim 1, wherein each of the superior endplate and the inferior endplate further includes a center housing formed between and in parallel with each corresponding endplate arm and coupled at one end to the corresponding endplate base, the superior endplate and the inferior endplate center housings forming a receptacle channel in between, wherein the receptacle of the actuation frame is guided by the receptacle channel when the actuation frame moves with respect to the face plate.

8. The method of claim 1, further comprising at least one tool keying recess and at least one tapped recess formed on the front surface of the face plate, wherein the at least one tool keying recess and the at least one tapped recess are formed so as to lock the spacer to a corresponding tool.

9. The method of claim 1, wherein the rear surface of the face plate includes a protrusion having the actuation channel passing through and guiding the body of the actuation screw, wherein the protrusion is further coupled to a hinge.

10. The method of claim 9, wherein the hinge comprises tabs located on an end of each endplate arm coupled to the rear surface of the face plate via pins, wherein the tabs are fastened, via the pins, to the rear surface of the face plate at corresponding pin recesses.

11. The method of claim 10, wherein the rear surface of the face plate is formed with a tapered wall to provide clearance for the hinge.

12. The method of claim 1, wherein each of the superior endplate and the inferior endplate have a recess formed in the endplate base to receive a knob formed on the frame base of the actuation frame.

13. The method of claim 1, wherein the superior endplate, the inferior endplate, and the actuation frame have generally U-shaped configurations with an area inside that form graft window regions, the graft window regions allowing for insertion of graft material within the variable lordotic interbody spacer.

14. A method of implanting a variable lordotic interbody spacer in a disc space between two adjacent vertebrae, the method comprising:
inserting the spacer in the disc space, the spacer comprising:
a face plate having a front surface and a rear surface, the face plate further having at least one actuation channel and at least two stabilizer channels formed through a portion of the face plate;
superior and inferior endplates, each of the endplates having proximal and distal ends and having first and second endplate arms coupled by an endplate base in a generally U-shaped configuration, each endplate arm coupled to the rear surface of the face plate via a hinge opposite from the base, and each endplate arm having a ramp recess on a top surface and a bottom surface;
an actuation frame positioned between the superior endplate and the inferior endplate, the actuation frame having first and second frame arms coupled by a frame base in a generally U-shaped configuration, each frame arm having a stabilizer opposite from the frame base and configured to pass through a corresponding stabilizer channel, each frame arm having an actuation ramp pin on a top surface and on a bottom surface fitted to a corresponding ramp recess, the actuation frame further including a receptacle formed at the inside of the frame base between each frame arm; and
an actuation screw having a head, body and threaded end, the actuation screw body passing through one of the at least one actuation channel, the head retained at the front surface and the threaded end threadably coupled to the receptacle of the actuation frame, and wherein the actuation screw is configured to be retained in the face plate by a screw plate retainer fastened to the front surface of the face plate, wherein the screw plate retainer is configured to allow rotation of the actuation screw within the face plate while otherwise preventing the actuation screw from changing position relative to the face plate; and
adjusting an angle between the superior endplate and the inferior endplate by rotating the actuation screw such that the distance between the distal ends of the superior and inferior endplates increases while the distance between the proximal ends of the superior and inferior endplates remains the same.

15. The method of claim 14, further comprising securing the face plate to at least one of the adjacent vertebrae with one or more bone screws.

* * * * *